Figure 1:
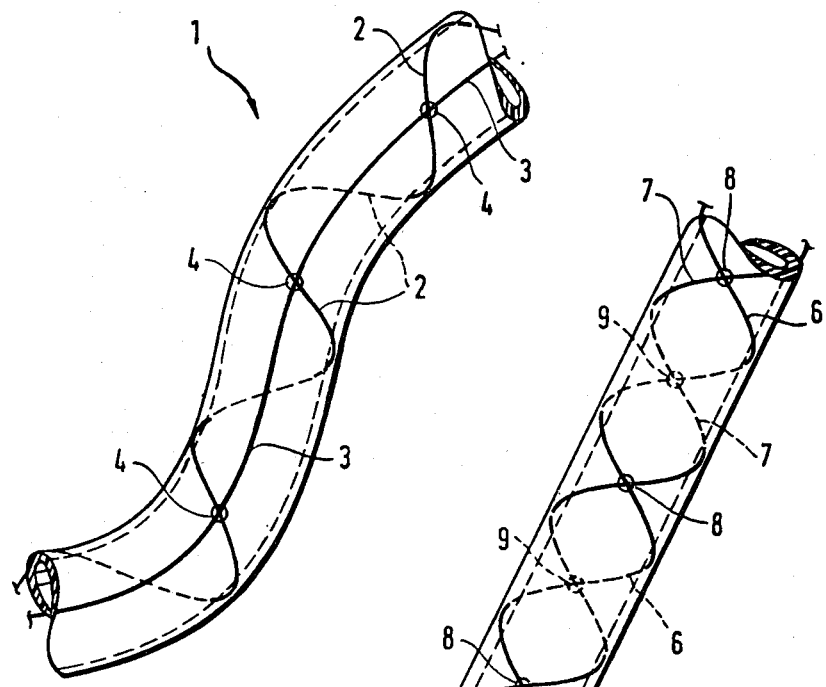

United States Patent [19]

Krütten

[11] 4,447,239

[45] May 8, 1984

[54] CATHETER WITH RADIOGRAPHIC CONTRAST STRIPS

[75] Inventor: Victor Krütten, St. Wendel, Fed. Rep. of Germany

[73] Assignee: Dr. Eduard Fresenius Chemisch-Pharmazeutishe Industry KG, Bad Homborg, Fed. Rep. of Germany

[21] Appl. No.: 375,190

[22] Filed: May 5, 1982

Related U.S. Application Data

[63] Continuation of Ser. No. 125,154, Feb. 27, 1980, abandoned.

[30] Foreign Application Priority Data

Mar. 19, 1979 [DE] Fed. Rep. of Germany ....... 2910741

[51] Int. Cl.³ .......................................... A61M 25/00
[52] U.S. Cl. ................................. 604/282; 128/419 P
[58] Field of Search ......... 604/21, 27, 19, 8, 158-173, 604/280, 282, 283-288; 128/419 P

[56] References Cited

U.S. PATENT DOCUMENTS

| | | | |
|---|---|---|---|
| 3,070,132 | 12/1962 | Sheridan | 128/348 |
| 3,485,234 | 12/1969 | Stevens | 128/2 |
| 3,509,883 | 5/1970 | Dibelius | 128/348 |
| 3,568,660 | 3/1971 | Crites | 128/419 P |
| 3,938,529 | 2/1976 | Gibbons | 128/348 |
| 4,073,287 | 2/1978 | Bradley et al. | 128/2 R |

FOREIGN PATENT DOCUMENTS 2553100 6/1976 Fed. Rep. of Germany .

Primary Examiner—C. Fred Rosenbaum
Assistant Examiner—T. J. Wallen
Attorney, Agent, or Firm—Hedman, Gibson, Costigan & Hoare

[57] ABSTRACT

A catheter is provided with a first radiographic contrast strip extending helically on or in the catheter wall with a constant pitch and a second such strip which is either disposed on a longitudinal generatrix of said wall to intersect said first strip once per convolution thereof or extends helically at the same constant pitch but in the opposite direction to intersect said first strip twice per convolution on respective opposite longitudinal generatrices.

12 Claims, 2 Drawing Figures

CATHETER WITH RADIOGRAPHIC CONTRAST STRIPS

This is a continuation of application Ser. No. 125,154 filed Feb. 27, 1980, now abandoned.

The invention relates to a catheter provided with radiographic contrast strips.

To enable one to follow on an X-ray screen the course of catheters introduced in veins or probes placed in the body of the patient, radiographic contrast strips are incorporated therein in the longitudinal direction. For the purpose of improving the radiographic distinctiveness, a plurality of contrast strips may be distributed over the hose circumference to extend longitudinally of the catheter or the probe.

When probe and catheters are applied, it is not only important to enable their course to be followed in the radiogram but also to permit one to determine the length to which the probes and catheters have been inserted. To ascertain the respective length of insertion of probes and catheters, it is known to apply colour markings on the surfaces of the hoses but in many cases these are difficult to discern. In addition, the colour markings can come off and are not compatible for the patient.

It is therefore the problem of the present invention to provide a probe or catheter of which the course and its length of application can be followed in the radiogram and determined therefrom.

According to the invention, this problem is solved in that one contrast strip helically extends in or on the surface of the catheter at a constant pitch and a second contrast strip of the same pitch extends correspondingly in the opposite direction so that the intersections of the contrast strips are disposed on a generatrix of the catheter. The respective length of application of the catheter, or of the probe in which the invention can be embodied in a corresponding manner, can be simply determined in the radiogram by counting the intersections of the oppositely extending helical contrast strips.

Since two intersections are produced on opposite generatrices of the hose for each convolution of the oppositely extending contrast strip helices, it may be desirable to locate one of the two contrast strips parallel to a generatrix of the hose so that it forms only one intersection with the helical contrast strip for each convolution of the latter. To determine the length of application, it is then only necessary to count the number of intersections and multiply this by the pitch of the helical contrast strip.

In a further embodiment of the invention, the contrast strips consist of insulated conductive material and are electrically connected to electrodes near the tip of the catheter and to terminals near its end. Probes or catheters constructed in this manner can be employed as pulse probe or catheters. If such a catheter is for example advanced right up to the heart, the contrast strips can be used as conductors leading pulses to the electrodes so that the activity of the heart can be stimulated by the pulses or defects in the rhythm of the heart can be corrected.

In a simple and desirable manner, the radiographic contrast strips can consist of wires of refined steel.

Figure 2:
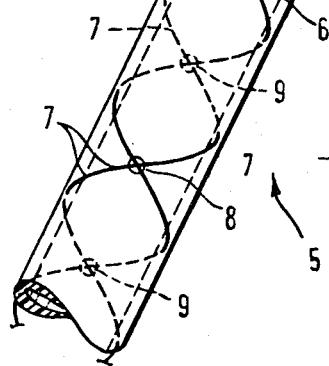

One example of the invention will now be described in more detail with reference to the drawing, wherein:

FIG. 1 is a plan view of part of a catheter or probe comprising a helical contrast strip and one extending parallel to the medial line, and FIG. 2 is a view similar to FIG. 1 with oppositely extending helical contrast strips.

FIG. 1 illustrates part of a hose 1 of a probe or catheter over the surface of which a helical contrast strip 2 extends at a constant pitch. Parallel to a generatrix of the hose 1 there is a second contrast strip 3 which forms intersections 4 with the helical contrast strip at the circled positions. The intersections 4 are therefore at a spacing from each other corresponding to the pitch of the helical contrast strip 2.

FIG. 2 shows part of the hose 5 of a catheter or a probe on the surface of which two contrast strip helices 6, 7 extend oppositely at a constant pitch. In this embodiment, two intersections are produced for each convolution of the contrast strips 6, 7, the circled intersections 8 being disposed on the upper generatrix and the intersections 9 which are circled in broken lines being disposed on the opposite lower generatrix.

The contrast strips 2, 3, 6, 7 may be located on the surface of the hose or be embedded therein so that the material of the hose will at the same time serve as insulation for the contrast strips if the latter are of conductive material.

I claim:

1. A catheter having first and second radiographic contrast strips in or on the surface of the catheter and having no additional contrast strips, the first said contrast strip being arranged in a helix along the length of the catheter with the helix of the first contrast strip defining a substantially constant pitch when the catheter is in use such that the first contrast strip intersects the second contrast strip at predetermined and equally spaced distances along the catheter, whereby when the catheter is inserted into a patient, the equally spaced intersections of the first and second contrast strips enable an accurate determination of the length of insertion of the catheter.

2. A catheter with first and second radiographic contrast strips as recited in claim 1, wherein the first contrast strip extends helically at a constant pitch along said catheter, and where the second contrast strip extends longitudinally along said catheter so that said contrast strips intersect one another once for each convolution of said catheter by said first contrast strip.

3. A catheter with first and second radiographic contrast strips as recited in claim 1 with the first contrast strip extending helically at a constant pitch along said catheter, and the second contrast strip extending helically along said catheter at a constant pitch equal to the pitch of the first said contrast strip, but with the second contrast strip being generated circumferentially in a direction opposite that of said first contrast strip.

4. A catheter as recited in claims 1, 2 or 3 wherein the contrast strips consist of insulated conductive material and are electrically connected to electrodes near the tip of the catheter and to terminals near its end.

5. A catheter as recited in claim 4 characterized in that the contrast strips are wires of refined steel.

6. A catheter as recited in claims 1, 2 or 3 characterized in that the contrast strips are wires of refined steel.

7. A probe having first and second radiographic contrast strips in or on the surface of the probe and having no additional contrast strips, the first said contrast strip being arranged in a helix along the length of the probe with the helix of the first contrast strip defining a substantially constant pitch when the probe is in use such that the first contrast strip intersects the second contrast strip at predetermined and equally spaced distances along the probe, whereby when the probe is inserted into a patient, the equally spaced intersections of the first and second contrast strips enable an accurate determination of the length of insertion of the probe.

8. A probe with first and second radiographic contrast strips as recited in claim 7, wherein the first contrast strip extends helically at a constant pitch along said probe, and where the second contrast strip extends longitudinally along said probe so that said contrast strips intersect one another once for each convolution of said probe by said first contrast strip.

9. A probe with first and second radiographic contrast strips as recited in claim 7 with the first contrast strip extending helically at a constant pitch along said probe, and the second contrast strip extending helically along said probe at a constant pitch equal to the pitch of the first said contrast strip, but with the second said contrast strip being generated circumferentially in a direction opposite that of said first contrast strip.

10. A probe as recited in claims 7, 3 or 9 wherein the contrast strips consist of insulated conductive material and are electrically connected to electrodes near the tip of the probe and to terminals near its end.

11. A probe as recited in claim 10 characterized in that the contrast strips are wires of refined steel.

12. A probe as recited in claims 7, 3 or 9 characterized in that the contrast strips are wires of refined steel.

* * * * *